United States Patent
Kobayashi et al.

(10) Patent No.: US 11,434,348 B2
(45) Date of Patent: Sep. 6, 2022

(54) CELLULOSE DERIVATIVE PARTICLES, COSMETIC COMPOSITION, AND METHOD FOR PRODUCING CELLULOSE DERIVATIVE PARTICLES

(71) Applicant: DAICEL CORPORATION, Osaka (JP)

(72) Inventors: Keiko Kobayashi, Tokyo (JP); Masaya Omura, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 152 days.

(21) Appl. No.: 16/818,619

(22) Filed: Mar. 13, 2020

(65) Prior Publication Data

US 2020/0299488 A1    Sep. 24, 2020

(30) Foreign Application Priority Data

Mar. 22, 2019 (JP) .............................. JP2019-054171

(51) Int. Cl.
| | | |
|---|---|---|
| *C08L 1/02* | (2006.01) | |
| *A61K 8/73* | (2006.01) | |
| *C08B 1/00* | (2006.01) | |
| *C08J 3/16* | (2006.01) | |
| *C08K 5/00* | (2006.01) | |

(52) U.S. Cl.
CPC .............. *C08L 1/02* (2013.01); *A61K 8/731* (2013.01); *C08B 1/003* (2013.01); *C08J 3/16* (2013.01); *C08K 5/0016* (2013.01)

(58) Field of Classification Search
CPC ...... C08L 1/02; C08L 1/10; C08L 1/14; C08L 1/28
See application file for complete search history.

(56) References Cited

U.S. PATENT DOCUMENTS

| | | | | | |
|---|---|---|---|---|---|
| 5,064,949 | A * | 11/1991 | Steiner | ................. | C08B 3/22 536/56 |
| 2004/0043964 | A1* | 3/2004 | Gomi | .................. | C08J 3/12 514/57 |
| 2004/0180067 | A1* | 9/2004 | Popplewell | ............. | C08L 1/28 424/401 |
| 2004/0180068 | A1* | 9/2004 | Popplewell | ............. | A23G 4/20 424/401 |
| 2005/0239925 | A1* | 10/2005 | Ito | ............................ | C08J 9/26 524/27 |
| 2007/0237956 | A1* | 10/2007 | Figuly | ................. | A61K 9/1635 428/402 |
| 2009/0170981 | A1 | 7/2009 | Ito | | |
| 2010/0178332 | A1* | 7/2010 | Kakizawa | ............ | A61K 9/2077 424/451 |
| 2010/0247914 | A1 | 9/2010 | Enomoto et al. | | |
| 2011/0282049 | A1* | 11/2011 | Shelton | ............... | C09D 175/04 536/58 |
| 2017/0114203 | A1* | 4/2017 | Narita | ....................... | C08J 9/24 |
| 2017/0144330 | A1* | 5/2017 | Ortega Andrade | ....... | B01J 2/08 |
| 2017/0226329 | A1* | 8/2017 | Malotky | .................. | C08J 3/122 |
| 2017/0275385 | A1* | 9/2017 | Capanema | .............. | C08H 6/00 |
| 2017/0292010 | A1* | 10/2017 | Malotky | .............. | A61K 9/2054 |
| 2018/0338927 | A1* | 11/2018 | Otsubo | ...................... | C08L 1/26 |
| 2019/0060238 | A1* | 2/2019 | Dormer | ................... | A61P 31/18 |
| 2020/0179261 | A1* | 6/2020 | Kobayashi | ............ | A61K 8/732 |

FOREIGN PATENT DOCUMENTS

| | | |
|---|---|---|
| EP | 3 613 794 A1 | 2/2020 |
| JP | 2004-51942 A | 2/2004 |
| JP | 2004-59611 A | 2/2004 |
| JP | 2009-137806 A | 6/2009 |
| JP | 2012-21119 A | 2/2012 |
| JP | 2016-500129 A | 1/2016 |
| JP | 6187653 B1 | 8/2017 |
| WO | WO 2014/066463 A1 | 5/2014 |

OTHER PUBLICATIONS

Edgar et al. (Prog. Polym. Sci. 26, 2001, 1605-1688) (Year: 2001).*
Extended European Search Report dated Aug. 24, 2020, in European Patent Application No. 20163867.3.
Office Action dated Oct. 5, 2021, in Japanese Patent Application No. 2019-054171.

* cited by examiner

*Primary Examiner* — Liam J Heincer
(74) *Attorney, Agent, or Firm* — Birch, Stewart, Kolasch & Birch, LLP

(57) ABSTRACT

Cellulose derivative particles including an alkoxy group having 2 or more carbons or an acyl group having 3 or more carbons, wherein the cellulose derivative particles have an average particle size of 80 nm or greater and 100 μm or less, a sphericity of 70% or greater and 100% or less, and a surface smoothness of 80% or greater and 100% or less; and a total substitution degree of the cellulose derivative is 0.7 or greater and 3 or less.

20 Claims, 2 Drawing Sheets

CELLULOSE DERIVATIVE PARTICLES, COSMETIC COMPOSITION, AND METHOD FOR PRODUCING CELLULOSE DERIVATIVE PARTICLES

TECHNICAL FIELD

The present invention relates to cellulose derivative particles, a cosmetic composition, and a method for producing cellulose derivative particles.

BACKGROUND ART

To date, various polymer fine particles according to the application have been proposed. For example, the purpose of fine particles contained in cosmetics also varies. The purpose of adding fine particles in cosmetics includes improving the spread of the cosmetic, changing the tactile sensation, imparting a wrinkle blurring effect, and improving the slipperiness of the product, such as a foundation.

In particular, fine particles having high sphericity are excellent in tactile sensation and provide a light scattering (soft focus) effect depending on the physical properties and shape thereof. Such fine particles when used in a foundation or the like fill and smooth the roughness of the skin to scatter the light in various directions, and thus an effect of making wrinkles and the like less noticeable (soft focus) can be expected.

For such a purpose and an effect of cosmetics, fine particles to be contained in cosmetics need to have a narrow particle size distribution and high sphericity. Such fine particles include fine particles made of a synthetic polymer, which have been proposed in the art, such as nylon 12; polymethyl methacrylate (PMMA); polystyrene (PS); polypropylene (PP); and polyethylene (PE).

However, among these synthetic polymers, fine particles made of PP, PE, or the like are light with a specific gravity of 1 or less and have too small particle size, thus easily float in water and may not be removed at a sewage treatment facility, and may flow as they are into the river and further into the sea through the river. Thus, there is a problem that the ocean and the like are contaminated with fine particles made of these synthetic polymers. Furthermore, fine particles made of PS, among synthetic polymers, contain a phthalate ester-based plasticizer, such as dioctyl phthalate, as the main plasticizer. Some phthalate ester-based plasticizers are suspected of being environmental hormones, and it is not preferred that they flow into the ocean.

Furthermore, fine particles made of these synthetic polymers have the property of adsorbing trace amounts of chemical contaminants in the environment, and this leads to concerns about various effects to be caused; for example, planktons and fish swallow fine particles that have adsorbed the chemical contaminants, which can also negatively affect the human body.

From such concerns, attempts have been made to replace fine particles of synthetic polymers used in various applications with other particles.

Cellulose or cellulose derivatives are excellent in that they can be obtained from natural materials, such as wood or cotton flowers, which do not compete with food or feed. Thus, it would be beneficial if fine particles of synthetic polymers can be substituted with fine particles of cellulose, which is a natural polymer, or a cellulose derivative, which is a semi-synthetic polymer. However, polymers to which a production method of fine particles of synthetic polymers can be applied are limited, and it is difficult to apply such a production method to production of fine particles of cellulose or a cellulose derivative.

Patent Document 1 describes a method including: forming a polysaccharide ester product from a polysaccharide synthesis, wherein the polysaccharide ester product contains a polysaccharide ester and a solvent; diluting the polysaccharide ester product and thereby forming a polysaccharide ester dope; and forming a plurality of polysaccharide ester microspheres from the polysaccharide ester dope; and describes a cosmetic composition as an article that can contain a polysaccharide ester microsphere.

Patent Document 2 describes a cellulose acylate having a volume average particle size D50 as measured using a laser diffraction particle size distribution measuring device of 72 μm or greater and 100 μm or less, a degree of polymerization of 131 or greater and 350 or less, and a substitution degree of 2.1 or greater and 2.6 or less; and also describes that a method for producing the cellulose acylate is preferably a method for producing a cellulose acylate, the method including: acylating cellulose in the presence of sulfuric acid; and deacylating the acylated cellulose in a polar solvent in the presence of acetic acid.

Patent Document 3 describes kneading a resin component (A), such as a thermoplastic resin, and a water soluble auxiliary component (B) to prepare a dispersion; and eluting the auxiliary component (B) from the dispersion to produce a molded article constituted of the resin component (A) (for example, a porous article or spherical particles); and also describes a cellulose derivative, such as a cellulose acetate, as the resin component (A).

CITATION LIST

Patent Document

Patent Document 1: JP 2016-500129 A
Patent Document 2: JP 6187653 B
Patent Document 3: JP 2004-051942 A

SUMMARY OF INVENTION

Technical Problem

However, the polysaccharide ester microspheres of Patent Document 1 are porous particles having a large particle size and a broad particle size distribution, and thus are not sufficient as an alternative to fine particles of synthetic polymers to be contained in products, such as cosmetics. In addition, the cellulose acylates obtained by the production method described in Patent Document 2 are also amorphous porous particles. Furthermore, the particulate molded article obtained by the production method described in Patent Document 3 also has a low sphericity and is particles that are approximately spherical. Thus, known fine particles have poor tactile sensation.

An object of the present invention is to provide fine particles containing a semi-synthetic polymer of a cellulose derivative and excellent in tactile sensation.

Solution to Problem

A first aspect of the present invention relates to cellulose derivative particles including an alkoxy group having 2 or more carbons or an acyl group having 3 or more carbons, wherein the cellulose derivative particles have an average particle size of 80 nm or greater and 100 μm or less, a sphericity of 70% or greater and 100% or less, and a surface smoothness of 80% or greater and 100% or less; and a total substitution degree of the cellulose derivative is 0.7 or greater and 3 or less.

In the cellulose derivative particles, the total substitution degree of the cellulose derivative may be 2.0 or greater and less than 2.6.

In the cellulose derivative particles, the acyl group may have 3 or more and 18 or less carbons.

In the cellulose derivative particles, the alkoxy group may have 2 or more and 8 or less carbons.

In the cellulose derivative particles, the true specific gravity may be 1.04 or greater.

In the cellulose derivative particles, the cellulose derivative particles may contain a plasticizer, and the content of the plasticizer may be greater than 0 wt. % and 40 wt. % or less relative to a weight of the cellulose derivative particles.

In the cellulose derivative particles, the plasticizer may be a glycerin ester-based plasticizer.

A second aspect of the present invention relates to a cosmetic composition containing cellulose derivative particles.

A third aspect of the present invention relates to a method for producing cellulose derivative particles, the method including: kneading a cellulose derivative having a total substitution degree of 0.7 or greater and 3 or less and a water-soluble polymer at 200° C. or higher and 280° C. or lower to obtain a dispersion containing the cellulose derivative as a dispersoid; and removing the water-soluble polymer from the dispersion.

In the method for producing cellulose derivative particles, the cellulose derivative having a total substitution degree of 0.7 or greater and 3 or less may be a cellulose derivative impregnated with a plasticizer; and the cellulose derivative impregnated with a plasticizer is a product formed by melt-kneading the cellulose derivative having a total substitution degree of 0.7 or greater and 3 or less and the plasticizer in a range of 20° C. or higher and lower than 200° C.

In the method for producing the cellulose derivative particles, the plasticizer may be a glycerin ester-based plasticizer.

In the method for producing the cellulose derivative particles, the plasticizer may be triacetin.

In the method for producing the cellulose derivative particles, the water-soluble polymer may be polyvinyl alcohol or thermoplastic starch.

Advantageous Effects of Invention

According to the present invention, fine particles containing a semi-synthetic polymer of a cellulose derivative and excellent in tactile sensation can be provided.

DESCRIPTION OF EMBODIMENTS

Cellulose Derivative Particles

Figure 1:
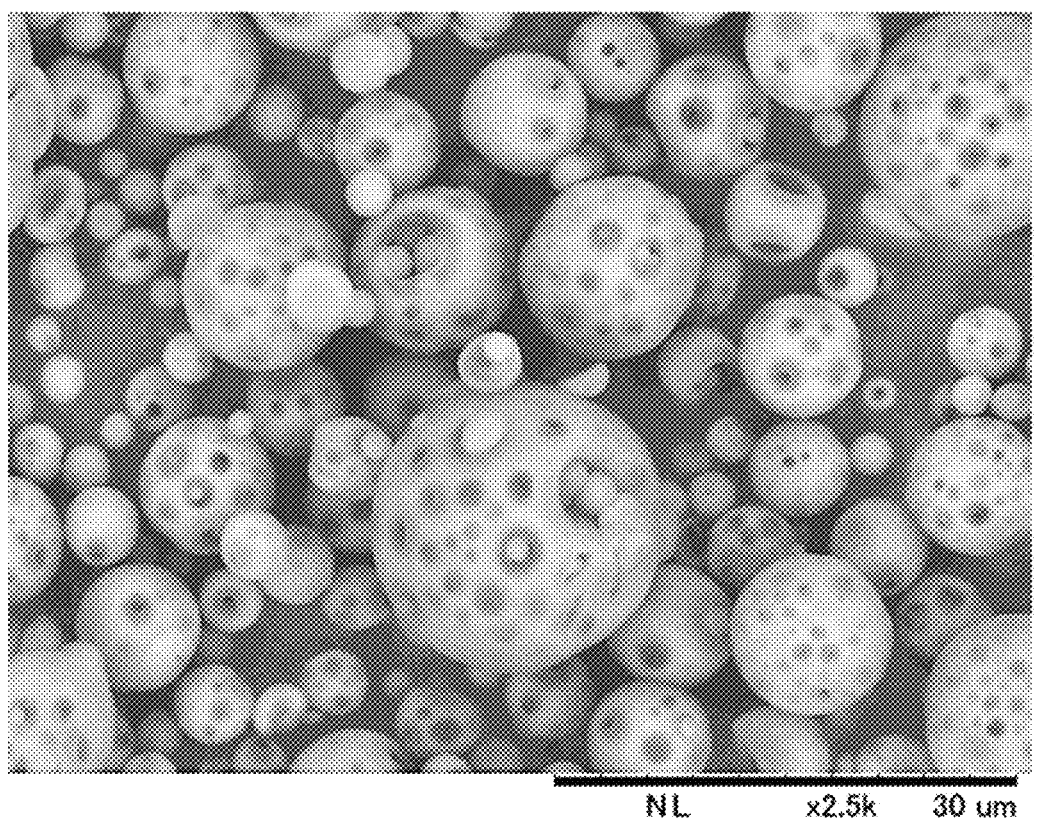
FIG. 1 is a drawing illustrating a method for evaluating surface smoothness (%).

Cellulose derivative particles of the present disclosure are cellulose derivative particles including an alkoxy group having 2 or more carbons or an acyl group having 3 or more carbons, wherein the cellulose derivative particles have an average particle size of 80 nm or greater and 100 µm or less, a sphericity of 70% or greater and 100% or less, and a surface smoothness of 80% or greater and 100% or less; and a total substitution degree of the cellulose derivative is 0.7 or greater and 3 or less.

The cellulose derivative particles including an alkoxy group having 2 or more carbons will be described. The number of carbons that the alkoxy group has is not particularly limited as long as the alkoxy group has 2 or more carbons, but the alkoxy group may have 3 or more, or 5 or more carbons. In addition, the alkoxy group may have 20 or less carbons and has preferably 8 or less carbons.

In addition, the cellulose derivative particles may include both an alkoxy group having 2 or more carbons and an alkoxy group having 1 carbon (a methoxy group).

Examples of the alkoxy group having 2 or more carbons include an ethoxy group, a protoxy group, a butoxy group, a pentoxy group, a hexoxy group, a heptoxy group, and an octoxy group.

The cellulose derivative particles including an acyl group having 3 or more carbons will be described. The number of carbons that the acyl group has is not particularly limited as long as the acyl group has 3 or more carbons, but the acyl group may have 4 or more, 10 or more, or 14 or more carbons. In addition, the alkoxy group may have 40 or less carbons and has preferably 18 or less carbons. The more carbons the acyl group has, the more increased flexibility the cellulose derivative particles have.

In addition, the cellulose derivative particles may include both an acyl group having 3 or more carbons and an acyl group having 2 carbons (an acetyl group).

Examples of the acyl group having 3 or more carbons include a propionyl group, a butyryl group, a pentanoyl (valeryl) group, a hexanoyl group, a heptanoyl group, an octanoyl group, a nonanoyl group, an undecanoyl group, a dodecanoyl group, a tridecanoyl group, a tetradecanoyl (myristoyl) group, a pentadecanoyl group, a hexadecanoyl group, a heptadecanoyl group, and an octadecanoyl (stearoyl) group.

The average particle size of the cellulose derivative particles of the present disclosure is 80 nm or greater and 100 µm or less, wherein the average particle size thereof may be 100 nm or greater, 1 µm or greater, 2 µm or greater, or 4 µm or greater. In addition, the average particle size may be 80 µm or less, 40 µm or less, 20 µm or less, or 14 µm or less. The cellulose derivative particles having a too large average particle size would have poor tactile sensation and a reduced light scattering (soft focus) effect. In addition, the cellulose derivative particles having a too small average particle size would be difficult to produce. Further, examples of the tactile sensation include skin feel and tactile sensation of a cosmetic composition containing the cellulose derivative particles, in addition to tactile sensation in directly touching the cellulose derivative particles.

The average particle size can be measured using dynamic light scattering, specifically as follows. First, a sample is prepared by forming the cellulose derivative particles in a concentration of 100 ppm into a pure water suspension using an ultrasonic vibrating device. Thereafter, the average particle size can be measured by measuring the volume frequency particle size distribution by laser diffraction ("Laser Diffraction/Scattering Particle Size Distribution Measurement Device LA-960" available from Horiba Ltd., ultrasonic treatment for 15 minutes, refractive index (1.500, medium (water; 1.333)). The average particle size herein refers to the value of the particle size corresponding to 50% of the integrated scattering intensity in this particle size distribution.

The coefficient of variation of the particle size of the cellulose derivative particles of the present disclosure may be 0% or greater and 60% or less, or 2% or greater and 50% or less.

The coefficient of variation (%) of the particle size can be calculated by: standard deviation of particle size/average particle size×100.

The sphericity of the cellulose derivative particles of the present disclosure is 70% or greater and 100% or less, preferably 80% or greater and 100% or less, more preferably 90% or greater and 100% or less, and still more preferably 95% or greater and 100% or less. The cellulose derivative particles with a sphericity less than 70% would have poor tactile sensation, and, for example, a cosmetic composition containing such cellulose derivative particles would have reduced soft focus effect.

The sphericity can be measured by the following method. Using an image of particles observed with a scanning electron microscope (SEM), the major axis and the minor axis of 30 randomly selected particles are measured to determine the minor axis/major axis ratio of each particle, and the average value of the minor axis/major axis ratios is taken as the sphericity (%). Here, it can be determined that the closer to 100% the sphericity is, the closer to the true sphere the particle is.

The surface smoothness of the cellulose derivative particles of the present disclosure is 80% or greater and 100% or less, preferably 85% or greater and 100% or less, more preferably 90% or greater and 100% or less. The cellulose derivative particles with a surface smoothness of less than 80% would have poor tactile sensation. The surface smoothness is preferably closer to 100% in terms of tactile sensation.

The surface smoothness can be determined by taking a scanning electron micrograph of the particles, observing the roughness of the particle surface, and being based on the area of a depressed portion therein.

The total substitution degree of the cellulose derivative of the cellulose derivative particles of the present disclosure is 0.7 or greater and 3 or less, preferably 1.0 or greater and 3 or less, more preferably 1.4 or greater and 3 or less, and still more preferably 2.0 or greater and 3 or less. This is because the cellulose derivative with such total substitution degree is excellent in moldability and easily produces spherical particles with high sphericity.

The cellulose derivative with a total substitution degree less than 0.7 would have increased water solubility and tend to elute in extracting particles in producing the cellulose derivative particles described below, particularly in removing a water-soluble polymer from a dispersion. This may reduce the sphericity of the resulting particles and thus may lead to poor tactile sensation. Note that the cellulose derivative with a total substitution degree closer to 3 would have poorer biodegradability.

The total substitution degree of the cellulose derivative can be measured by the following method. First, the total substitution degree of the cellulose derivative is the sum of each substitution degree at the 2-, 3-, and 6-positions of the glucose ring of the cellulose derivative, and each substitution degree at the 2-, 3-, and 6-positions of the glucose ring of the cellulose derivative can be measured by NMR according to the method of Tezuka (Tezuka, Carbonydr. Res. 273, 83 (1995)). That is, the free hydroxyl group of the cellulose derivative is acylated with a carboxylic anhydride in pyridine. The type of the carboxylic anhydride used here should be selected according to the purpose of the analysis; for example, when the propionyl substitution degree of cellulose acetate propionate is analyzed, acetic anhydride is suitable, and when the acetyl substitution degree is analyzed, propionic anhydride is suitable. The solvent and the acid anhydride of the acylation reaction may be appropriately selected according to the cellulose derivative to be analyzed.

A sample obtained by acylation is dissolved in deuteriochloroform and the $^{13}$C-NMR spectrum is measured. For example, when the substituent is an acetyl group, a propionyl group, or a butyryl group, the carbon signals of the acetyl group appear in the region from 169 ppm to 171 ppm in the order of the 2-, 3-, and 6-positions from the high magnetic field; the carbonyl carbon signals of the propionyl group appear in the region from 172 ppm to 174 ppm in the same order; and the carbon signals of the butyryl group appear likewise in the region from 171 ppm to 173 ppm in the order of the 2-, 3-, and 6-positions from the high magnetic field side. In another example, when a cellulose derivative including a propionyl group or a cellulose derivative including no propionyl group is treated with propionic anhydride for an analytical purpose, and the propionyl substitution degree is analyzed, the carbonyl carbon signals of the propionyl group appear in the region from 172 ppm to 174 ppm in the same order.

The total substitution degree of the cellulose derivative treated with the anhydrous carboxylic acid by the method of Tezuka or a method similar thereto is 3.0, and thus if a total sum of the areas of the carbonyl carbon signal of the acyl group originally included in the cellulose derivative and the carbonyl signal of the acyl group introduced by the carboxylic anhydride treatment is normalized to 3.0, and the presence ratio of the acetyl group and the propionyl group at each corresponding position (area ratio of each signal) is determined, each acyl substitution degree at the 2-, 3-, and 6-positions of the glucose ring in the original cellulose derivative can be determined. It goes without saying, a substituent containing an acyl group that can be analyzed by this method is only a substituent group that does not correspond to the carboxylic anhydride used in the treatment for an analytical purpose.

However, in a case where it is known in advance that the total substitution degree of the 2-, 3-, and 6-positions of the glucose ring of the cellulose derivative of a sample is 3.0, and all the substituents thereof are limited to substituents, such as an acetyl group and a propionyl group, the NMR spectrum can be measured by dissolving the sample directly in deuteriochloroform without acylation. In a case where all the substituents are an acetyl group and a propionyl group, the carbon signals of the acetyl group appears in the region from 169 ppm to 171 ppm in the order of 2-, 3-, and 6-positions from high magnetic field, and the carbon signals of the propionyl group appears in the region from 172 ppm to 174 ppm in the same order, as in the case including acylation, and thus the substitution degree, such as each of acetyl and propionyl substitution degrees at the 2-, 3-, and 6-positions of the glucose ring in the cellulose derivative, can be determined from the presence ratio of the acetyl group and the propionyl group at each corresponding position (in other words, the area ratio of each signal).

The cellulose derivative particles of the present disclosure may have a bulk specific gravity of 0.1 or greater and 0.9 or less, 0.5 or greater and 0.9 or less, or 0.6 or greater and 0.9 or less. For example, when the particles are contained in a cosmetic, the higher the bulk specific gravity of the particles, the better the flowability of the cosmetic composition. The bulk specific gravity can be measured by a method in accordance with JIS K 1201-1.

The cellulose derivative particles of the present disclosure have a true specific gravity of preferably greater than 1, more preferably 1.04 or greater, still more preferably 1.1 or greater, and most preferably 1.2 or greater. In terms of obtaining the cellulose derivative fine particles having the sphericity of 70% or greater, the true specific gravity may be 1.35 or less. The true specific gravity can be measured by 2. Measurement Method with Pycnometer (liquid:water) of JIS Z 8807-1976 "Solid Specific Gravity Measurement Method".

The true specific gravity is the specific gravity based on the density of water of 0.999973 g/cm$^{-3}$ at 4° C.

The cellulose derivative particles of the present disclosure may or may not contain a plasticizer. In the present disclosure, the plasticizer refers to a compound capable of increasing the plasticity of the cellulose derivative. The plasticizer is not particularly limited, and examples thereof include adipate-based plasticizers containing an adipate ester, such as dimethyl adipate, dibutyl adipate, diisostearyl adipate, diisodecyl adipate, diisononyl adipate, diisobutyl adipate, diisopropyl adipate, diethylhexyl adipate dioctyl adipate, dioctyldodecyl adipate, dicapryl adipate, and dihexyldecyl adipate; citrate-based plasticizers containing a citrate ester, such as acetyl triethyl citrate, acetyl tributyl citrate, isodecyl citrate, isopropyl citrate, triethyl citrate, triethylhexyl citrate, and tributyl citrate; glutarate-based plasticizers containing a glutarate ester, such as diisobutyl glutarate, dioctyl glutarate, and dimethyl glutarate; succinate-based plasticizers containing a succinate ester, such as diisobutyl succinate, diethyl succinate, diethylhexyl succinate, and dioctyl succinate; sebacate-based plasticizers containing a sebacate ester, such as diisoamyl sebacate, diisooctyl sebacate, diisopropyl sebacate, diethyl sebacate, diethylhexyl sebacate, and dioctyl sebacate; glycerin ester-based plasticizers containing a glycerin alkyl ester, such as triacetin, diacetin, and monoacetin; neopentyl glycol; and phosphate-based plasticizers containing a phosphate ester, such as trioleil phosphate, tristearyl phosphate, and tricetyl phosphate. These plasticizers may be used alone, or two or more thereof may be used in combination.

Among them, preferred are at least one or more plasticizers selected from the group consisting of citrate-based plasticizers containing a citrate ester, such as triethyl citrate, acetyl triethyl citrate, and acetyl tributyl citrate; glycerin ester-based plasticizers containing a glycerin alkyl ester, such as triacetin, diacetin, and monoacetin; and adipate-based plasticizers, such as diisononyl adipate; more preferred are at least one or more plasticizers selected from the group consisting of triethyl citrate, acetyl triethyl citrate, acetyl tributyl citrate, triacetin, and diisononyl adipate; and still more preferred are at least one or more selected from the group consisting of acetyl triethyl citrate, triacetin, and diacetin. A phthalate-based plasticizer can be used, but it must be used with care because of concerns about similarity to environmental hormones.

When the cellulose derivative particles contain a plasticizer, the content of the plasticizer contained in the cellulose derivative particles is not particularly limited. For example, the plasticizer may be contained, relative to the weight of the cellulose derivative particles, in an amount of greater than 0 wt. % and 40 wt. % or less, 0.01 wt. % or greater and 40 wt. % or less, 0.05 wt. % or greater and 35 wt. % or less, 0.1 wt. % or greater and 30 wt. % or less, 0.4 wt. % or greater and 20 wt. % or less, 0.4 wt. % or greater and 15 wt. % or less, 0.4 wt. % or greater and 10 wt. % or less, 0.4 wt. % or greater and 5 wt. % or less, or 0.4 wt. % or greater and 2.5 wt. % or less. The less content of the plasticizer, the better, but a larger content may be acceptable as long as it does not impair the object of the present invention.

The content of the plasticizer in the cellulose derivative particles is determined by $^{1}$H-NMR measurement by dissolving the cellulose derivative particles in a solvent capable of dissolving the cellulose derivative particles.

The cellulose derivative particles of the present disclosure can be produced by a production method described below.

The cellulose derivative particles of the present disclosure are excellent in tactile sensation and thus can be suitably used, for example, in cosmetic compositions. In addition, they have high sphericity, and thus cellulose derivative particles, when contained in a cosmetic composition, fill and smooth the roughness of the skin to scatter the light in various directions, thereby providing an effect of making wrinkles and the like less noticeable (soft focus).

Examples of the cosmetic composition include foundations, such as liquid foundations and powder foundations; concealers; sunscreens; makeup bases; lipsticks and lipstick bases; white makeup powders, such as body powders, solid white powders, and face powders; solid powder eye shadows; wrinkle masking creams; and skin and hair external preparations mainly for cosmetic purposes, such as skin care lotions; and the dosage form thereof is not limited. The dosage form may be any of a liquid preparation, such as an aqueous solution, a milky lotion, or a suspension; a semi-solid preparation, such as a gel and a cream; or a solid preparation, such as a powder, a granule, and a solid. In addition, the dosage form may be an emulsion preparation, such as a cream and a milky lotion; an oil gel preparation, such as a lipstick; a powder preparation, such as a foundation; an aerosol preparation, such as a hair styling agent; or the like.

The cosmetic composition containing the cellulose derivative particles of the present disclosure, particularly the liquid foundation, has excellent spread to the skin, covering power for spots and freckles, and slipperiness.

Method for Producing Cellulose Derivative Particles

A method for producing cellulose derivative particles of the present disclosure includes: kneading a cellulose derivative having a total substitution degree of 0.7 or greater and 3 or less and a water-soluble polymer at 200° C. or higher and 280° C. or lower to obtain a dispersion containing the cellulose derivative as a dispersoid; and removing the water-soluble polymer from the dispersion.

Preparation of Dispersion

Preparation of the dispersion includes kneading a cellulose derivative having a total substitution degree of 0.7 or greater and 3 or less and a water-soluble polymer at 200° C. or higher and 280° C. or lower to obtain a dispersion containing the cellulose derivative as a dispersoid.

The kneading of the cellulose derivative and the water-soluble polymer can be performed with an extruder, such as a twin-screw extruder. The temperature of the kneading refers to the cylinder temperature.

The dispersion may be extruded in a string shape from a die attached to the tip of an extruder, such as a twin-screw extruder, and then cut into pellets. At this time, the die temperature may be 220° C. or higher and 300° C. or lower.

The total substitution degree of the cellulose acetate is 0.7 or greater and 3 or less, preferably 1.0 or greater and 3 or less, more preferably 1.4 or greater and 3 or less, and still more preferably 2.0 or greater and 3 or less. The total substitution degree can be adjusted by adjusting the conditions of aging (conditions, such as time and temperature).

The water-soluble polymer may be contained in an amount of 55 parts by weight or greater and 99 parts by weight or less relative to 100 parts by weight of the total amount of the cellulose derivative and water-soluble polymer, preferably 60 parts by weight or greater and 90 parts by weight or less, and still more preferably 65 parts by weight or greater and 85 parts by weight or less.

The water-soluble polymer in the present specification refers to a polymer having an insoluble content of less than 50 wt. % when 1 g of the polymer is dissolved in 100 g of water at 25° C. Examples of the water-soluble polymer may include polyvinyl alcohol, polyethylene glycol, sodium polyacrylate, polyvinylpyrrolidone, polypropylene oxide, polyglycerin, polyethylene oxide, vinyl acetate, modified starch, thermoplastic starch, methyl cellulose, ethyl cellulose, hydroxyethyl cellulose, and hydroxypropyl cellulose. Among them, polyvinyl alcohol, polyethylene glycol, and thermoplastic starch are preferred, and polyvinyl alcohol and thermoplastic starch are particularly preferred. Further, the thermoplastic starch can be obtained by a well-known method. For example, reference can be made to JP 06-6307 B, WO92/04408, etc., and more specifically, for example, a thermoplastic starch prepared by mixing approximately 20% of glycerin as a plasticizer to tapioca starch and kneading them with a twin-screw extruder can be used.

The resulting dispersion is a dispersion containing the water-soluble polymer as a dispersion medium and the cellulose derivative as a dispersoid. In other words, the dispersion may be a constitution containing the water-soluble polymer as a sea component and the cellulose derivative as an island component. In the dispersion, the kneaded product constituting the island component contains the cellulose derivative and is mainly spherical.

The cellulose derivative having a substitution degree of 0.7 or greater and 3 or less can be produced by a well-known method for producing the derivative. When the cellulose derivative is a cellulose ester, it can be produced, for example, through activating a raw material pulp (cellulose); acylating the activated cellulose with an esterifying agent (acylating agent); deactivating the acylating agent after the completion of the acylation reaction; and aging (saponifying, hydrolyzing) the produced cellulose acylate. In addition, the method may include pretreating the raw material pulp to disintegrate/grind it and then to spray and mix acetic acid therewith prior to the activation. The method may include post-treating the resulting cellulose acylate to precipitate and separate, purify, stabilize, and dry it after the aging (saponifying, hydrolyzing).

In addition, when the cellulose derivative is a cellulose ether, it can be produced through immersing a raw material pulp (cellulose) in a mixture of a lower aliphatic alcohol, such as isopropyl alcohol (IPA) or tertiary butanol (TBA), water, and an alkali metal hydroxide, such as sodium hydroxide, to obtain an alkali cellulose, which is a precursor of the cellulose ether; and further adding an etherifying agent and slurrying (precipitating). Furthermore, the method may include pretreating the raw material pulp to disintegrate/grind it and then to spray and mix acetic acid therewith prior to obtaining the alkali cellulose. The method may include post-treating the resulting cellulose ether to precipitate and separate, purify, stabilize, and dry it after slurrying (precipitating) the cellulose ether.

Removal of Water-Soluble Polymer

The removal of the water-soluble polymer from the dispersion will be described.

The method for removing the water-soluble polymer is not particularly limited as long as the water-soluble polymer can be dissolved and removed from the particles, but examples thereof include a method of dissolving and removing the water-soluble polymer of the dispersion using a solvent, such as water; an alcohol, such as methanol, ethanol, or isopropanol; or a mixture thereof. Specifically, examples thereof include a method of removing the water-soluble polymer from the dispersion, such as by mixing the dispersion and the solvent and filtering the mixture to take out the filtrate.

As described below, when the cellulose derivative having a total substitution degree of 0.7 or greater and 3 or less and a plasticizer are mixed to prepare the cellulose derivative impregnated with a plasticizer prior to obtaining the dispersion, the plasticizer may or may not be removed from the dispersion together with the water-soluble polymer. Thus, the resulting cellulose derivative particles may or may not contain a plasticizer.

The mixing ratio of the dispersion and the solvent is preferably 0.01 wt. % or greater and 20 wt. % or less, more preferably 2 wt. % or greater and 15 wt. % or less, and still more preferably 4 wt. % or greater and 13 wt. % or less of the dispersion, relative to the total weight of the dispersion and the solvent. If the dispersion is higher than 20 wt. %, the water-soluble polymer would not be sufficiently dissolved and could not be removed by washing, or it would be difficult to separate the cellulose derivative particles not dissolved in the solvent and the water-soluble polymer dissolved in the solvent by an operation, such as filtration or centrifugation.

The mixing temperature of the dispersion and the solvent is preferably 0° C. or higher and 200° C. or lower, more preferably 20° C. or higher and 110° C. or lower, and still more preferably 40° C. or higher and 80° C. or lower. At temperatures lower than 0° C., the water-soluble polymer would not be sufficiently dissolved and would be difficult to remove by washing, and at temperatures higher than 200° C., deformation, aggregation, or the like of the particles would occur, and it would be difficult to take out the particles while maintaining the desired shape of the particles.

The mixing time of the dispersion and the solvent is not particularly limited and may be appropriately adjusted, but may be, for example, for 0.5 hours or longer, for 1 hour or longer, for 3 hours or longer, or for 5 hours or longer, and for 6 hours or shorter.

In addition, the method of mixing is not limited as long as the water-soluble polymer can be dissolved, but the water-soluble polymer can be efficiently removed from the dispersion even at room temperature by using, for example, a stirring device, such as an ultrasonic homogenizer or a three-one motor.

For example, when a three-one motor is used as the stirring device, the rotation number during mixing the dispersion and the solvent may be, for example, 5 rpm or greater and 3000 rpm or less. The water-soluble polymer can thereby be more efficiently removed from the dispersion. In addition, this also results in efficiently removing the plasticizer from the dispersion.

Optional Preparation of Cellulose Derivative Impregnated with Plasticizer

The cellulose derivative having a total substitution degree of 0.7 or greater and 3 or less may be a cellulose derivative impregnated with a plasticizer, and the method may include mixing the cellulose derivative having a total substitution degree of 0.7 or greater and 3 or less and a plasticizer to obtain the cellulose derivative impregnated with the plasticizer prior to obtaining the dispersion. In preparation of the cellulose derivative impregnated with a plasticizer, the cellulose derivative having a total substitution degree of 0.7 or greater and 3 or less and a plasticizer are mixed.

The plasticizer is not particularly limited, and any plasticizer having a plasticizing effect in melt-extruding the cellulose derivative can be used. Specifically, the plasticizer exemplified as a plasticizer contained in the cellulose derivative particles can be used alone or in combination of two or more plasticizers.

Among the exemplified plasticizers, preferred are at least one or more plasticizers selected from the group consisting of citrate-based plasticizers containing a citrate ester, such as triethyl citrate, acetyl triethyl citrate, and acetyl tributyl citrate; glycerin ester-based plasticizers containing a glycerin alkyl ester, such as triacetin, diacetin, and monoacetin; and adipate-based plasticizers, such as diisononyl adipate; more preferred are at least one or more plasticizers selected from the group consisting of triethyl citrate, acetyl triethyl citrate, acetyl tributyl citrate, triacetin, diacetin, and diisononyl adipate; and still more preferred are at least one or more plasticizers selected from the group consisting of acetyl triethyl citrate, triacetin, and diacetin. A phthalate-based plasticizer must be used with care because of concerns about similarity to environmental hormones.

The plasticizer may be contained in an amount of greater than 0 parts by weight and 40 parts by weight or less, 2 parts by weight or greater and 40 parts by weight or less, 10 parts by weight or greater and 30 parts by weight or less, or 15 parts by weight or greater and 20 parts by weight or less, relative to 100 parts by weight of the total amount of the cellulose derivative and the plasticizer. If the amount is too small, the sphericity of the resulting cellulose derivative particles would tend to decrease, and if the amount is too large, the shape of the particles could not be maintained, resulting in a decreasing tendency of the sphericity.

The cellulose acetate derivative and the plasticizer can be dry-mixed or wet-mixed using a mixer, such as a Henschel mixer. When a mixer, such as a Henschel mixer, is used, the temperature within the mixer may be a temperature at which the cellulose derivative does not melt, for example, in a range of 20° C. or higher and lower than 200° C.

In addition, the cellulose derivative and the plasticizer may be mixed by melt-kneading. Furthermore, the melt-kneading may be performed in combination with mixing using a mixer, such as a Henschel mixer, and in this case, the melt-kneading is preferably performed after mixing in temperature conditions in a range of 20° C. or higher and lower than 200° C. using a mixer, such as a Henschel mixer. The plasticizer and the cellulose derivative become more uniform and compatible in a short period of time, thereby increasing the sphericity of the cellulose derivative particles that can be finally prepared, and improving the tactile sensation and touch feeling thereof.

The melt-kneading is preferably performed by heating and mixing with an extruder. The kneading temperature (cylinder temperature) of the extruder may be in a range of 200° C. to 230° C. Even at temperatures in this range, a uniform kneaded product can be obtained. At too low temperatures, the sphericity of the resulting particles would decrease, and thus the tactile sensation and the touch feeling would decrease. At too high temperatures, deterioration or coloration of the kneaded product due to heat may occur. In addition, the viscosity of the melted material decreases, and thus kneading of the resin in a twin-screw extruder could be insufficient.

The melting point of the cellulose derivative depends on the substitution degree but is approximately from 230° C. to 280° C. and is close to the decomposition temperature of the cellulose derivative. Thus, melt kneading is typically difficult in this temperature range, but the cellulose derivative (flakes) impregnated with the plasticizer can reduce the plasticizing temperature. The kneading temperature (cylinder temperature) may be, for example, 200° C. when a twin-screw extruder is used. The kneaded product may be extruded in a strand shape and formed into a pellet form by hot cutting or the like. The die temperature in this case may be approximately 220° C.

EXAMPLES

Hereinafter, the present invention will be described specifically with reference to examples, but the technical scope of the present invention is not limited by these examples.

Example A-1

First, 100 parts by weight of cellulose acetate propionate (CAP-482-0.5 available from Eastman Chemical) and 10 parts by weight of triacetin as a plasticizer were fed to a twin-screw extruder (PCM30 available from Ikegai Corp, cylinder temperature of 200° C., die temperature of 220° C.) equipped with a liquid adding device, melt-kneaded, extruded, and pelletized to prepare a kneaded product.

Then, 30 parts by weight of the pellets of the resulting kneaded product and 70 parts by weight of polyvinyl alcohol (available from The Nippon Synthetic Chemical Industry Co., Ltd., melting point of 190° C., saponification degree of 99.1%) as a water-soluble polymer were blended in a dry state, then fed to a twin-screw extruder (PCM30 available from Ikegai Corp, cylinder temperature of 220° C., die temperature of 220° C.), and extruded to form a dispersion.

The resulting dispersion was combined with pure water (solvent) to give a concentration of 5 wt. % or less (weight of dispersion/(weight of dispersion+weight of pure water)× 100), and the mixture was stirred using a three-one motor (BL-3000 available from Shinto Scientific Co., Ltd.) at a rotation number of 100 rpm, at a temperature of 80° C. for 3 hours. The solution after stirring was filtered off with filter paper (No. 5A available from ADVANTEC), and the filtrate was taken out. An operation of preparing the resulting filtrate using pure water again was performed to give a concentration of the dispersion of 5 wt. % or less, further stirring the mixture at a rotation number of 100 rpm, at a temperature of 80° C. for 3 hours, and filtering off the solution to take out the filtrate was repeated three or more times to obtain cellulose derivative particles (cellulose acetate propionate particles). The resulting cellulose derivative particles were determined to have a total substitution degree of 2.58 (acetyl substitution degree of 0.18 and propionyl substitution degree of 2.40) as the substitution degrees thereof were determined by measuring $^1$H-NMR thereof.

The average particle size, the coefficient of variation of the particle size, the sphericity, the surface smoothness, the bulk specific gravity, the plasticizer content, the true specific gravity, and the tactile sensation of the resulting cellulose derivative particles were each measured and evaluated. The results are shown in Table 1. Each physical property was measured and evaluated by the methods described below.

Average Particle Size and Coefficient of Variation of Particle Size

The average particle size was measured using dynamic light scattering. First, the sample was adjusted to a concentration of approximately 100 ppm using pure water, and a pure water suspension was prepared using an ultrasonic vibrating device. Thereafter, the volume frequency particle size distribution was determined by laser diffraction ("Laser Diffraction/Scattering Particle Size Distribution Measurement Device LA-960" available from Horiba Ltd., ultrasonic treatment for 15 minutes, refractive index (1.500, medium (water; 1.333)), and the average particle size was measured. The average particle size (nm and μm, or the like) herein was the value of the particle size corresponding to 50% of the integrated scattering intensity in the volume frequency particle size distribution. In addition, the coefficient of variation (%) of the particle size was calculated by: standard deviation of particle size/average particle size×100.

Sphericity

Using an image of particles observed with a scanning electron microscope (SEM), the major axis and the minor axis of 30 randomly selected particles were measured to determine the minor axis/major axis ratio of each particle, and the average value of the minor axis/major axis ratios was taken as the sphericity.

Surface Smoothness

Figure 2:
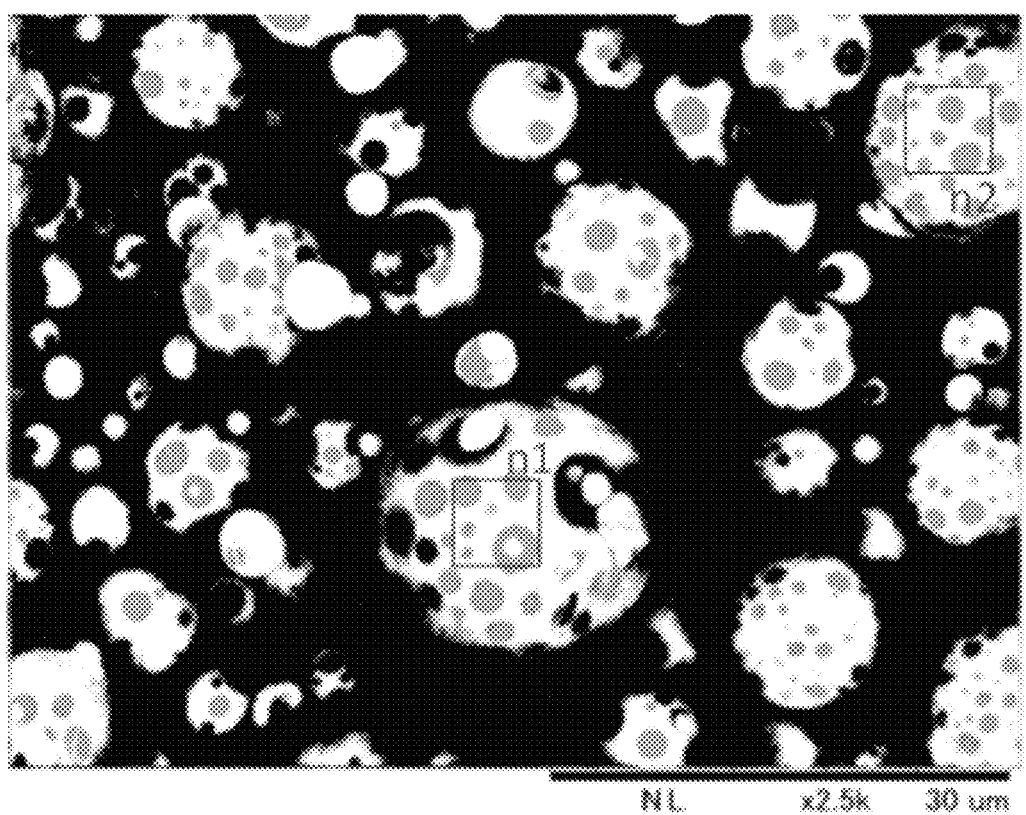
FIG. 2 is a drawing illustrating a method for evaluating surface smoothness (%).

A scanning electron micrograph of the particles was taken at a magnification of 2500 to 5000× (see FIG. 1 for an example of a micrograph of cellulose derivative particles), and the image was binarized using an image processing device WinROOF (available from Mitani Corporation) (See FIG. 2 for the binarized image of the micrograph of FIG. 1). It may be any area smaller than the particle including the center and/or the vicinity of the center of one particle (for example, the areas indicated by n1 and n2 in FIG. 2). In addition, the size of the area may be 5 μm square when the particle size is 15 μm. The area percentage of the portion corresponding to a depression (the shaded portion) in a roughness in the area is calculated, and the surface smoothness (%) of the one particle is calculated by the following formula.

Surface smoothness (%) of one particle=(1−area ratio of depression)×100

Area ratio of depression=area of depressed portion in the any area/the any area

The surface smoothness (%) was the average value of the surface smoothness of randomly selected 10 particle samples, that is, n1 to 10. The higher this numerical value, the higher the surface smoothness is.

Bulk Specific Gravity

The bulk specific gravity was measured according to "JIS K 1201-1".

Plasticizer Content

The plasticizer content (wt. %) was measured by $^1$H-NMR measurement.

True Specific Gravity

The true specific gravity was measured by 2. Measurement Method with Pycnometer (liquid:water) of JIS Z 8807-1976 "Solid Specific Gravity Measurement Method".

Tactile Sensation

Sensory evaluation was performed according to a panel test by 20 panelists for the tactile sensation of the particles. Panelists were allowed to touch the particles to evaluate comprehensively both smoothness and moist feeling on a maximum score of 5 points according to the following criteria, and an average score from 20 panelists was calculated.

Good: 5. Slightly good: 4. Average: 3. Slightly poor: 2. Poor: 1.

Example A-2

Cellulose derivative particles (cellulose acetate propionate particles) were obtained in the same manner as in Example A-1 with the exception that a plasticizer was not added, the pellets of the resulting kneaded product were changed to 20 parts by weight, and polyvinyl alcohol was changed to 80 parts by weight. The resulting cellulose derivative particles were determined to have a total substitution degree of 2.58 (acetyl substitution degree of 0.18 and propionyl substitution degree of 2.40) as the substitution degrees thereof were determined by measuring $^1$H-NMR thereof.

Example A-3

Cellulose derivative particles (cellulose acetate butyrate particles) were obtained in the same manner as in Example A-2 with the exception that cellulose acetate propionate was changed to cellulose acetate butyrate (CAB-171-15 available from Eastman Chemical). The resulting cellulose derivative particles were determined to have a total substitution degree of 3.11 (acetyl substitution degree of 2.04 and butyryl substitution degree of 0.71) as the substitution degrees thereof were determined by measuring $^1$H-NMR thereof.

Example A-4

Cellulose stearate particles were obtained in the same manner as in Example A-2 with the exception that cellulose acetate propionate was changed to cellulose stearate (C18) obtained by the following synthesis method.

Synthesis Method of Cellulose Stearate

To a 100-L reaction vessel equipped with a stirrer, a reflux condenser, a thermometer, and a dropping funnel, 486 g of cellulose and 30 kg of pyridine were added, followed by addition of 3450 g of stearic acid chloride. The temperature of the mixture was increased to a temperature range of 80° C. to 100° C. under a nitrogen atmosphere, and the mixture was allowed to react by continuously stirring for 12 hours.

After completion of the reaction, the reaction mixture was charged to 90 kg of methanol, and the target crude cellulose derivative was precipitated.

The precipitated crude cellulose derivative was filtered out, and washing with methanol and separation by filtration were repeated three times. The filtrate was then vacuum-dried at 90° C. for 8 hours, and 2120 g of the target cellulose derivative particles was obtained. The substitution degree of the resulting cellulose derivative particles (cellulose stearate particles) was determined to be 3.0 by measuring $^1$H-NMR thereof.

Example A-5

Cellulose derivative particles (cellulose myristilate particles) were obtained in the same manner as in Example A-4 with the exception that 3450 g of stearate chloride was changed to 2881 g of myristic acid chloride ($C_{14}H_{27}COCl$). The weight of the resulting cellulose derivative particles was 2211 g, and the substitution degree thereof was 3.0.

Example A-6

Ethyl cellulose particles were obtained in the same manner as in Example A-2 with the exception that cellulose acetate propionate was changed to ethyl cellulose (Ethocel Std. 10 available from Dow Chemical Co., Ltd.).

Example A-7

Methyl octyl cellulose particles were obtained in the same manner as in Example A-2 with the exception that cellulose acetate propionate was changed to methyl octyl cellulose obtained by the following synthesis method.

Synthesis of Methyl Octyl Cellulose

To a 100-L reaction vessel equipped with a stirrer, a reflux condenser, a thermometer, and a dropping funnel, 2000 g of methyl cellulose (available from FUJIFILM Wako Pure Chemical Corporation, methyl substitution degree of 1.8) and 40 L of dimethylacetamide were added and stirred at room temperature. Then, 5000 g of powdered sodium hydroxide was added to the mixture, and the mixture was stirred as it was for 1 hour. After the mixture was returned to room temperature, 2 L of octyl iodide was added dropwise to the mixture, the mixture was stirred at room temperature for 30 minutes, then allowed to react by stirring at 50° C. for 5 hours.

After completion of the reaction, the reaction mixture was returned to room temperature. To the reaction vessel 240 L of methanol was charged while the reaction mixture therein was being vigorously stirred to precipitate a white solid. The white solid was filtered out by pressure filtration, and then washed twice with water. The white solid was dried by heating at 80° C. for 12 hours, and 2100 g of the target cellulose derivative was obtained. The resulting cellulose derivative (methyl octyl cellulose) was determined to have a total substitution degree of 2.10 (methyl substitution degree of 1.8 and octyl substitution degree of 0.3) as the substitution degrees thereof were determined by measuring $^1$H-NMR thereof.

Each physical property of the cellulose derivative particles obtained in each example was evaluated according to the measurement methods described above. The results are shown in Table 1.

Comparative Example A-1

Toray Nylon (trademark) Nylon 12 SP-500 (available from Toray Industries, Inc.) was used as nylon particles. Each physical property of the particles was evaluated according to the measurement methods described above. The results are shown in Table 1.

Comparative Example A-2

Matsumoto Microsphere (trademark) M-100 (available from Matsumoto Yushi-Seiyaku Co., Ltd.) was used as acrylic particles. Each physical property of the particles was evaluated according to the measurement methods described above. The results are shown in Table 1.

Comparative Example A-3

Celluflow TA-25 (available from JNC) was used as cellulose acetate particles. Each physical property of the particles was evaluated according to the measurement methods described above. The results are shown in Table 1.

Comparative Example A-4

Celluflow C-25 (available from JNC) was used as cellulose particles. Each physical property of the particles was evaluated according to the measurement methods described above. The results are shown in Table 1.

TABLE 1

|  | Example A-1 Cellulose acetate propionate particles | Example A-2 Cellulose acetate propionate particles | Example A-3 Cellulose acetate butylate particles | Example A-4 Cellulose stearate particles | Example A-5 Cellulose myristilate particles | Example A-6 Ethyl cellulose particles | Example A-7 Methyl octyl cellulose particles |
|---|---|---|---|---|---|---|---|
| Total substitution degree (DS) | 2.58 | 2.58 | 3.11 | 3.0 | 3.0 | 2.50 | 2.10 |
| Each substitution degree | Acetyl substitution degree: 0.18 Propionyl substitution degree: 2.40 | Acetyl group: 0.18 Propionyl group: 2.40 | Acetyl group: 2.40 Butyryl group: 0.71 | — | — | — | Methyl group: 1.80 Octyl group: 0.3 |
| Plasticizer | Triacetin | — | — | — | — | — | — |
| Average particle size (μm) [μm] | 10.2 | 9.5 | 8.2 | 5.2 | 3.8 | 7.7 | 5.1 |
| Coefficient of variation of particle size [%] | 35 | 34 | 38 | 33 | 36 | 38 | 36 |
| Sphericity [%] | 97 | 95 | 96 | 97 | 96 | 97 | 95 |
| Surface smoothness [%] | 100 | 100 | 100 | 100 | 100 | 100 | 100 |
| Bulk specific gravity | 0.66 | 0.63 | 0.64 | 0.70 | 0.71 | 0.64 | 0.67 |
| Plasticizer content [wt. %] | 0.5 | — | — | — | — | — | — |
| True specific gravity | 1.23 | 1.23 | 1.26 | 0.98 | 0.99 | 1.15 | 1.12 |
| Tactile sensation | 4.3 | 4.4 | 4.3 | 4.6 | 4.2 | 4.5 | 4.1 |

TABLE 1-continued

|  | Comparative Example A-1 Nylon particles | Comparative Example A-2 Acrylic particles | Comparative Example A-3 Cellulose acetate particles | Comparative Example A-4 Cellulose particles |
|---|---|---|---|---|
| Total substitution degree (DS) | — | — | 2.85 | — |
| Plasticizer | — | — | — | — |
| Average particle size (μm) [μm] | 5.0 | 8.1 | 7.3 | 9.2 |
| Coefficient of variation of particle size [%] | 32 | 35 | 38 | 37 |
| Sphericity [%] | 96 | 95 | 91 | 90 |
| Surface smoothness [%] | 100 | 100 | 72 | 68 |
| Bulk specific gravity | 0.53 | 0.61 | 0.33 | 0.38 |
| Plasticizer content [wt. %] | — | — | — | — |
| True specific gravity | 1.02 | 1.19 | 1.28 | 1.52 |
| Tactile sensation | 4.5 | 3.5 | 2.7 | 3.1 |

As shown in Table 1, all the cellulose derivative particles of the examples are semi-synthetic polymers and have excellent tactile sensation.

Example B-1

Preparation of Liquid Foundation

Each component shown Table 2 was mixed, then stirred well, and the mixture was filled into a container to prepare a liquid foundation. Each physical property of the resulting liquid foundation was evaluated by the methods described below. The results are shown in Table 3.

TABLE 2

| Component | Product name, etc. | wt. % |
|---|---|---|
| Coconut oil alkyl caprylate | Cetiol C5 (BASF) | 10.2 |
| Undecane/tridecane | Cetiol Ultimate (BASF) | 5.0 |
| Mineral oil | Hicall K-230 (Kaneda Co., Ltd.) | 5.0 |
| Ethylhexyl methoxycinnamate | Uvinul MC80 (BASF F) | 4.0 |
| Isononyl isononanoate | KAK-99 (Kokyu Alcohol Kogyo Co., Ltd.) | 3.0 |
| Disteardimonium hectorite, cyclopentasiloxane, other | Bentone Gel VS-5 PC V HV (Elementis) | 3.0 |
| Macademia Nut Fatty Acid Phytosteryl | Plandool-MAS (Nippon Fine Chemical Co., Ltd.) | 0.3 |
| Trimethylsiloxysilicate, polypropylsilsesquioxane | MQ-1640 Flake Resin (Dow Corning Toray Co., Ltd.) | 0.3 |
| PEG-10 Dimethicone | KF-6017P (Shin-Etsu Chemical Co., Ltd.) | 1.5 |
| Polyglyceryl oleate-2, polyhydroxystearic acid, polyglyceryl stearate-2 | PolyAquol OS2 (innovacos) | 1.0 |
| Titanium oxide, cyclopentasiloxane, other | SDL-Ti70 (Daito Kasei Kogyo Co., Ltd.) | 10.3 |
| Mica | Y2300 (Yamaguchi Mica Co., Ltd.) | 1.0 |
| Boron nitride | SHP-6 (Mizushima Ferroalloy Co., Ltd.) | 1.0 |
| Iron oxide, cyclopentasiloxane, other | SDL-IOY50 (Daito Kasei Kogyo Co., Ltd.) SDL-IOR50 (Daito Kasei Kogyo Co., Ltd.) SDL-IO0B5 (Daito Kasei Kogyo Co., Ltd.) | 3.0 |
| Cellulose derivative particles obtained in Example A-1 | | 3.0 |
| BG | 1,3-BG (Daicel Corporation) | 4.0 |
| Pentylene glycol | Diol PD (Kokyu Alcohol Kogyo Co., Ltd.) | 2.0 |
| Phenoxy ethanol | Phenoxyethanol-SP (Yokkaichi Chemical Co., Ltd.) | 0.3 |
| Sodium chloride | | 1.0 |
| EDTA-2Na | | 0.03 |
| Purified water | | Remaining amount |
| Total | | 100.0 |

Spread to Skin

A tactile measurement device (static-kinetic friction measurement device TL201Ts) was used to measure the length of spread of 0.2 g of the liquid foundation per run.

Covering Power

A small amount of the liquid foundation was applied to the skin, and the degree of hiding spots and freckles was evaluated according to the following criteria by spreading the liquid foundation with a finger 20 times.

Excellent: sufficiently covered

Good: covered

Marginal: covered but insufficient

Fail: no covering power

Uniformity

A small amount of the liquid foundation was applied to the skin, and the uniformity was evaluated according to the following criteria by spreading the liquid foundation with a finger 20 times.

Excellent: uniformly spread

Good: uniform

Marginal: slightly speckled

Fail: speckled

Slipperiness

A small amount of the liquid foundation was applied to the skin, and the slipperiness (creaminess) was evaluated according to the following criteria by spreading the liquid foundation with a finger 20 times.

Excellent: well slippery and sufficiently creamy
Good: well slippery and creamy
Marginal: poorly slippery
Fail: not slippery Examples B-2 to 7

A liquid foundation was prepared in the same manner as in Example B-1 with the exception that the cellulose derivative particles obtained in Example A-1 in Table 2 were changed to the cellulose derivative particles each obtained in Examples A-2 to 7. Each physical property of the resulting liquid foundation was evaluated by the methods described above. The results are shown in Table 3.

Comparative Examples B-1 to 4

A liquid foundation was prepared in the same manner as in Example B-1 with the exception that the cellulose derivative particles obtained in Example A-1 in Table 2 were changed to the particles each in Comparative Examples A-1 to 4. Each physical property of the resulting liquid foundation was evaluated by the methods described above. The results are shown in Table 3.

TABLE 3

|  | Example B-1 | Example B-2 | Example B-3 | Example B-4 | Example B-5 | Example B-6 |
|---|---|---|---|---|---|---|
| Spread to skin [mm] | 43 | 52 | 56 | 54 | 48 | 49 |
| Covering power | Excellent | Excellent | Good | Excellent | Excellent | Good |
| Uniformity | Excellent | Excellent | Good | Good | Excellent | Excellent |
| Slipperiness (creaminess) | Good | Excellent | Excellent | Excellent | Good | Good |

|  | Example B-7 | Comparative Example B-1 | Comparative Example B-2 | Comparative Example B-3 | Comparative Example B-4 |
|---|---|---|---|---|---|
| Spread to skin [mm] | 51 | 32 | 19 | 15 | 18 |
| Covering power | Excellent | Good | Marginal | Marginal | Fail |
| Uniformity | Good | Marginal | Fail | Fail | Fail |
| Slipperiness (creaminess) | Excellent | Good | Fail | Marginal | Marginal |

As shown in Table 3, all the cosmetic compositions containing the cellulose derivative particles of Examples B-1 to 8 are excellent in spread to the skin, covering power for spots and freckles, and slipperiness.

The invention claimed is:

1. Cellulose derivative particles comprising an alkoxy group having 2 or more carbons or an acyl group having 3 or more carbons,
   wherein the cellulose derivative particles have an average particle size of 80 nm or greater and 100 µm or less, a sphericity of 90% or greater and 100% or less, and a surface smoothness of 80% or greater and 100% or less; and
   a total substitution degree of the cellulose derivative is 0.7 or greater and 3 or less.

2. The cellulose derivative particles according to claim 1, wherein the total substitution degree of the cellulose derivative is 2.0 or greater and less than 2.6.

3. The cellulose derivative particles according to claim 2, wherein the acyl group has 3 or more and 18 or less carbons.

4. The cellulose derivative particles according to claim 2, wherein the alkoxy group has 2 or more and 8 or less carbons.

5. The cellulose derivative particles according to claim 2, wherein a true specific gravity is 1.04 or greater.

6. The cellulose derivative particles according to claim 2,
   wherein the cellulose derivative particles contain a plasticizer, and
   a content of the plasticizer is greater than 0 wt. % and 40 wt. % or less relative to a weight of the cellulose derivative particles.

7. The cellulose derivative particles according to claim 1, wherein the acyl group has 3 or more and 18 or less carbons.

8. The cellulose derivative particles according to claim 7, wherein the alkoxy group has 2 or more and 8 or less carbons.

9. The cellulose derivative particles according to claim 7, wherein a true specific gravity is 1.04 or greater.

10. The cellulose derivative particles according to claim 1, wherein the alkoxy group has 2 or more and 8 or less carbons.

11. The cellulose derivative particles according to claim 10, wherein a true specific gravity is 1.04 or greater.

12. The cellulose derivative particles according to claim 1, wherein a true specific gravity is 1.04 or greater.

13. The cellulose derivative particles according to claim 1,
   wherein the cellulose derivative particles contain a plasticizer, and
   a content of the plasticizer is greater than 0 wt. % and 40 wt. % or less relative to a weight of the cellulose derivative particles.

14. The cellulose derivative particles according to claim 13, wherein the plasticizer is a glycerin ester-based plasticizer.

15. A cosmetic composition containing the cellulose derivative particles according to claim 1.

16. A method for producing cellulose derivative particles according to claim 1, the method comprising the steps of:
   mixing a plasticizer and a cellulose derivative having a total substitution degree of 0.7 or greater and 3 or less and containing an alkoxy group having 2 or more carbons or an acyl group having 3 or more carbons to obtain a cellulose derivative impregnated with the plasticizer;

kneading the cellulose derivative impregnated with the plasticizer and a water-soluble polymer at 200° C. or higher and 280° C. or lower to obtain a dispersion containing the water-soluble polymer as a dispersion medium and the cellulose derivative as a dispersoid; and removing the water-soluble polymer from the dispersion, wherein the water-soluble polymer is selected from the group consisting of polyvinyl alcohol, polyethylene glycol, sodium polyacrylate, polyvinylpyrrolidone, polypropylene oxide, polyglycerin, polyethylene oxide, vinyl acetate, modified starch, thermoplastic starch, methyl cellulose, ethyl cellulose, hydroxyethyl cellulose, and hydroxypropyl cellulose.

17. The method for producing cellulose derivative particles according to claim 16,
wherein the step of mixing the cellulose derivative and the plasticizer to obtain the cellulose derivate impregnated with the plasticizer is conducted by melt-kneading at a temperature in a range of 20° C. or higher and lower than 200° C.

18. The method for producing cellulose derivative particles according to claim 17, wherein the plasticizer is a glycerin ester-based plasticizer.

19. The method for producing cellulose derivative particles according to claim 17, wherein the plasticizer is triacetin.

20. The method for producing cellulose derivative particles according to claim 16, wherein the water-soluble polymer is polyvinyl alcohol or thermoplastic starch.

* * * * *